(12) United States Patent
Herold et al.

(10) Patent No.: US 7,039,226 B2
(45) Date of Patent: May 2, 2006

(54) METHOD AND APPARATUS FOR MODELING MOMENTARY CONDITIONS OF MEDICAL OBJECTS DEPENDENT ON AT LEAST ONE TIME-DEPENDENT BODY FUNCTION

(75) Inventors: Gerold Herold, Erlangen (DE); Michael Scheuering, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 673 days.

(21) Appl. No.: 10/119,161

(22) Filed: Apr. 9, 2002

(65) Prior Publication Data
US 2003/0015207 A1    Jan. 23, 2003

(30) Foreign Application Priority Data
Apr. 9, 2001   (DE)   ................. 101 17 751

(51) Int. Cl.
*G06K 9/00*   (2006.01)
(52) U.S. Cl. .................. 382/131; 382/154; 600/425
(58) Field of Classification Search ............... 382/128, 382/131, 132, 154, 277, 285, 286, 302, 308, 382/107, 106; 703/2, 11; 433/25; 600/416, 600/425; 128/922; 356/39; 377/10; 250/363.04
See application file for complete search history.

(56) References Cited

U.S. PATENT DOCUMENTS

| 4,416,552 | A | * | 11/1983 | Hessemer et al. | .......... | 374/117 |
|---|---|---|---|---|---|---|
| 4,562,843 | A | * | 1/1986 | Djordjevich et al. | ........ | 600/485 |
| 5,515,856 | A | | 5/1996 | Olstad et al. | | |
| 6,757,423 | B1 | * | 6/2004 | Amini | ......................... | 382/154 |
| 2001/0024516 | A1 | * | 9/2001 | Yoshioka et al. | ........... | 382/128 |
| 2001/0047131 | A1 | * | 11/2001 | Maki et al. | .................. | 600/407 |
| 2002/0156364 | A1 | * | 10/2002 | Madore | ...................... | 600/410 |
| 2002/0193693 | A1 | * | 12/2002 | Kramarenko | ............... | 600/509 |
| 2003/0203016 | A1 | * | 10/2003 | Suwelack et al. | ........... | 424/449 |
| 2003/0233118 | A1 | * | 12/2003 | Hui | ........................... | 606/201 |
| 2004/0039267 | A1 | * | 2/2004 | Kawasaki et al. | .......... | 600/310 |
| 2004/0171939 | A1 | * | 9/2004 | May et al. | ................... | 600/481 |
| 2004/0264628 | A1 | * | 12/2004 | Besson | ......................... | 378/5 |
| 2005/0254708 | A1 | * | 11/2005 | Jolly et al. | ................. | 382/173 |
| 2005/0259864 | A1 | * | 11/2005 | Dickinson et al. | .......... | 382/154 |

FOREIGN PATENT DOCUMENTS

EP        0 660 252       12/1993

* cited by examiner

*Primary Examiner*—Barry Choobin
(74) *Attorney, Agent, or Firm*—Schiff Hardin LLP (57) ABSTRACT

In an apparatus and a method for modeling momentary conditions of a medical object dependent on at least one time-variable body function, at least one further status value of the time-variable body function is calculated on the basis of the geometry of the medical object that is acquired from data obtained with a medical imaging method for at least one status value of the time-variable body function, and the geometry of the medical object is made available approximately synchronously with the currently measured status value of the time-variable body function.

17 Claims, 6 Drawing Sheets

METHOD AND APPARATUS FOR MODELING MOMENTARY CONDITIONS OF MEDICAL OBJECTS DEPENDENT ON AT LEAST ONE TIME-DEPENDENT BODY FUNCTION

BACKGROUND OF THE INVENTION

1. Field of the Invention

The present invention is directed to a method and an apparatus for medical data processing to calculate the geometries of medical objects from data obtained by medical imaging, wherein an adaptation of static geometries to dynamic events is made. In particular, the present invention is directed to a method and an apparatus for the adaptation of pre-operatively measured, static data to intra-operative, dynamic events.

2. Description of the Prior Art

Imaging medical analysis devices are an indispensable part of medical diagnostics and are a critical basis for careful planning of operations. Tomographic methods supply three-dimensional data of the inside of the body that are converted into spatially surveyable views impressions of the inside of the body with modern methods of medical image processing. The planning of surgical interventions as well as therapeutic measures is facilitated because relevant anatomical structures such as, for example, nerves or fat tissue, bones or tissue equivalent to muscles as well as non-anatomical structures such as, for example, foreign bodies or implants are either isolated from the surroundings that have only secondary informational content, or are shown clearly delineated therefrom.

At present, measurements of patients in real time cannot be undertaken with medical imaging analysis devices. At present, only static exposures of medical objects of the type described above are therefore obtained from the measurements, i.e. rigid exposures of anatomical as well as of non-anatomical structures. The geometrical structures derived therefrom are consequently rigid objects. These objects, however, are not truly representative of the real medical objects they describe, a majority of which such as, for example, organs, change in shape dependent on the body position and, above all, dependent on body functions such as, for example, heart activity, respiration or intestinal peristalsis. The pre-operatively measured, rigid data are therefore only briefly and seldom in geometrical coincidence with the actual geometry of the dynamically deformed medical objects that they represent. Consequently, a superimposition of pre-operatively measured data with intra-operatively obtained image data such as, for example, in an image fusion with endoscopy or ultrasound images, will always lead to a more or less disturbing mismatch. Pre-operatively measured, rigid geometries also cannot be employed in navigation systems or for a robot control since they do not track the variation of the objects dependent on their underlying body functions.

SUMMARY OF THE INVENTION

It is an object of the present invention to provide a method and an apparatus that bring pre-operatively measured, medical image data into coincidence with intra-operative situations.

This object is inventively achieved in a method for modeling momentary conditions of a medical object dependent on at least one time-variable body function, wherein a first geometry of a medical object is calculated for at least one first status value of a time-variable body function proceeding from data acquired from a medical imaging method, and at least one further, second geometry of the medical object is calculated for a further, second status value of the time -variable body function, the second status value being different from the first status value, and a calculated geometry, whose underlying status value approximately corresponds to a currently measured status value of the body function is offered during the subsequent measurement of status values of the time-variable body function.

The above object also is achieved in an apparatus for modeling momentary conditions of a medical object dependent on at least one time-variable body function, having a first calculating device for calculating a first geometry of a medical object for at least one first status value of a time-variable function from data obtained by a medical imaging method, a second calculating device for calculating at least one further, second geometry of the medical object for a further, second status value of the time-variable body function, the second status value differing from the first status value, a reception device for receiving at least one measured value characterizing in the current status value of the time-variable body function, and a transmission device for transmitting the calculated geometry of the medical object to a further-processing device during the measurement of status values of the time-variable body function, with a currently measured status value of the body function at least approximately coinciding with the status value of the body function underlying the transmitted, calculated geometry.

The above object is also achieved by a computer software product for execution on a computer that has program instructions for the implementation of the inventive method described above.

The static geometry of a medical object obtained from a medical imaging method thus can be advantageously rendered dynamic, i.e. the geometry of a medical object that changes analogously to one or more time-variable body functions is available dependent on the time curve of these body functions, synchronized with the current variation of the geometry of the medical object itself. Also advantageously, pre-operative measured data can be brought into coincidence with intra-operatively obtained data, for example for an image fusion with endoscopy or ultrasound images. Likewise advantageously, coordinates coinciding with the real situation can now be transmitted from the modified geometries to navigation systems and robotic controls.

In an embodiment of the present invention, the first geometry of the medical object is calculated from data having a three-dimensional character that are acquired with a medical imaging method. The first geometry of the medical object can also be calculated from data from medical imaging methods having a two-dimensional character, so that a broad variety of pre-operative examination methods can be utilized for the acquisition of the object geometries.

In another embodiment of the invention, the further, second geometry is calculated for a further, second status value of the time-variable body function by interpolation from two existing geometries of the medical object. An adaptation of the geometry to inter-operative conditions is thus possible with little calculating outlay and with a precision that suffices for many applications.

In a preferred embodiment of the invention, the further, second geometry of the medical object is determined for a further, status condition value of the time-variable body function using a calculating model of the behavior of the object. Thus, knowledge about the functioning of, for example, implants, such as heart valves, or knowledge about the sequence of organ modifications such as, for example, the beating of the heart, can be advantageously utilized for a precise calculation of the variation of the geometry of the medical objects.

In a further embodiment of the present invention, the further, second geometry of the medical object is calculated for the further, second status value of the time-variable body function from an existing geometry of the medical object by means of morphing. The characteristic features for the geometry variation thus can be advantageously selected and can form the basis as prescriptions for the geometrical transformation.

Heart activity and/or respiration can form the basis as time-variable body function or functions for the variation of the geometry of the medical object, since these exert a specific influence on the variation of the geometry of many anatomical and non-anatomical structures.

DESCRIPTION OF THE PREFERRED EMBODIMENTS

Many body functions such as, for example, respiration and heart activity, exhibit a periodic course in a first approximation. This means that specific values of the body function re-occur with a certain regularity. In contrast to the strict mathematical meaning of periodic, as used herein "periodic body functions" does not require that the course of the body function repeat exactly at identical time intervals, but instead describes the behavior of a body function whose characteristics repeat at more or less uniform time intervals. The duration of such a time interval can shorten or lengthen in turn over the course of time, as is the case, for example, given accelerated or retarded respiration. In general, it is not only the time duration between two equivalent values of a body function that is variable; rather, the absolute values thereof are also subject to fluctuations.

Figure 1:
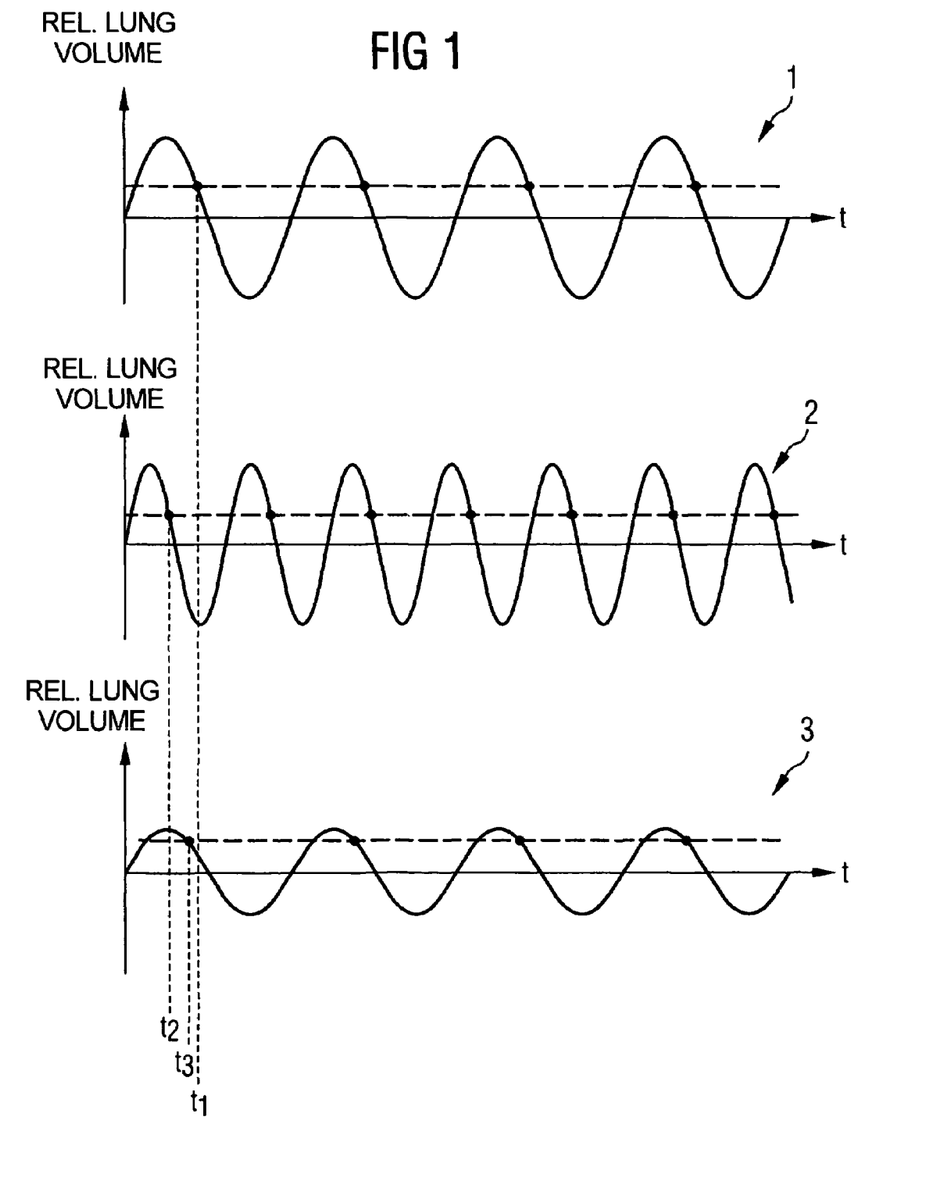
FIG. 1 schematically shows the time curve of a body function with—in a first approximation—periodically re-occurring values for various frequencies and amplitudes of this body function, with marked points indicating equivalent statuses of the body function.

This is schematically shown in FIG. 1 for respiration. When it is assumed that a medical object such as, for example, an organ is deformed due to respiration, then this object will have a very similar shape at the marked points. The points mark conditions having an identical lung volume and a distinction is made between inspiration and expiration, so that the dynamic influences on the object shape are also the same. This is not only true of normal respiration, as represented by the upper diagram 1 of FIG. 1, but can also be transferred to accelerated respiration—represented by the middle diagram 2 of FIG. 1—so that the aforementioned medical object in this case also has the same geometrical shape at the marked points as during normal respiration. Given shallow respiration as shown in the lower diagram 3 of FIG. 1, the quantity of air inhaled is reduced and thus the medical object influenced as a result thereof is also deformed to a lesser extent. Even if the respiratory frequency in shallow respiration were to correspond to that during normal respiration, the deformation corresponding to the marking occurs at a different, earlier point in time $t_3$.

It should be noted that not only does the organ defining the body function change its shape, but also other anatomical as well as non-anatomical structures are influenced in terms of their geometry by this body function. For example, the respiratory function not only influences the momentary shape of the lung that produces it, but also influences the position and shape of the vascular system and the organs in the abdominal cavity. Likewise, it is not only the shape of a heart that changes in the rhythm of the pulse but also the shape of arteries, and the condition of an artificial heart valve (if present).

When there is a functional dependency between one or more body functions and the geometry of a medical object, then the corresponding geometry of this object for every value of a body function or of a combination of body functions can be calculated from existing geometries for specific values of this body function or combination of body functions.

Figure 2:
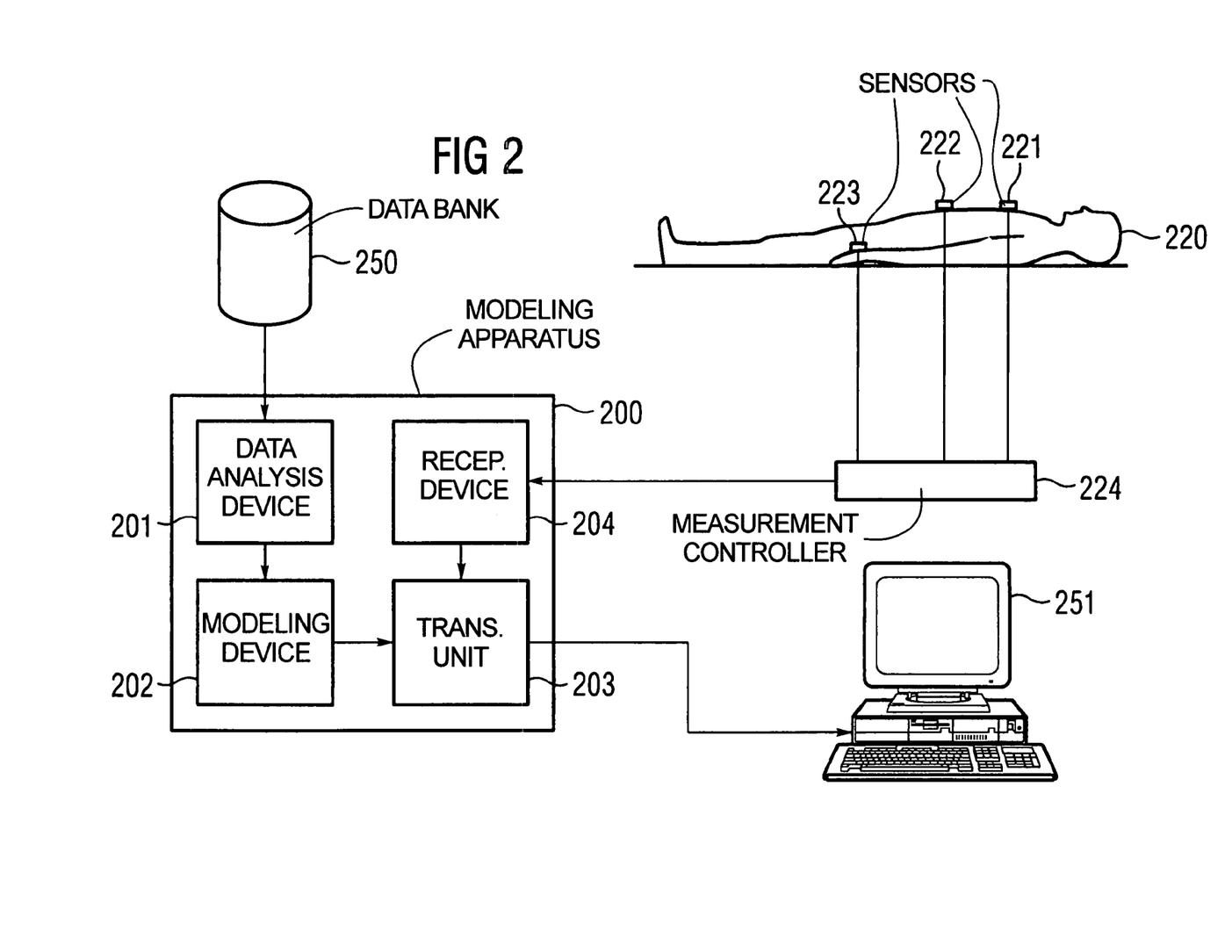
FIG. 2 schematically shows an apparatus of the present invention for modeling momentary conditions of medical objects.

FIG. 2 provides an overview of the apparatus for the implementation of the inventive method. The apparatus 200 for modeling momentary conditions of one or more medical objects has a data analysis device 201 that edits data relating to the geometries of medical objects supplied from a data storage unit 250 the data having been obtained from medical, imaging methods such that the geometry of at least one medical object can be extracted for at least one status value of the time-variable body function that influences the medical object. Since the objects of the medical interest are of a physical nature, they have calculated geometries of a three-dimensional character. Advantageously, the data obtained from the data storage unit 250 therefore also have a three-dimensional character; however, this is not compulsory. As set forth below, a three-dimensional geometry of the object can also be produced with the data analysis device 201 from two-dimensional views of an object in the same condition but from different viewing directions.

Let it also be assumed that the geometries of a medical object are influenced not only by an individual body function but by a number of body functions. For a clearer presentation of the invention, a single body function or a status value of a body function shall be discussed below, but the discussion is equally applicable to values of a number of body functions or a value of a combination of body functions.

In the modeling device 202 of the inventive apparatus, new geometries are calculated on the basis of the object geometries calculated in the data analysis device 20. These new geometries are valid for defined conditions or status values of the body function influencing the object. A number of methods can be employed for calculating these intermediate shapes.

When, for example, the calculated initial geometries represent the shape of the medical object for extreme conditions of the body function, then further intermediate shapes can be obtained on the basis of a simple, linear interpolation between these extreme geometries. In a weighted interpolation is used, i.e. an interpolation that is based on the time curve of the status values of the body function, a greater precision is achieved in the simulation of the object deformation. Additionally, a greater precision can be achieved by using supporting points for the geometries and if more precise interpolation is carried out between these points by morphing. The best results for calculating the intermediate shapes are achieved by employing calculation models representing the behavior of the medical object or its deformation dynamics. These models can, for example, be spring models on the basis which the deformation of the surface can be calculated accurately dependent on dislocations of a point or of a few points of the surface. Which method is employed in a specific case is dependent on the precision that is required for the respective employment. For a mere visualization of the data, a lower precision demand is usually established than for the employment of the data for controlling a surgical robot or for utilization of the data in a navigation system.

Coordinated with the current condition value of the underlying body function, the calculated, new geometries are forwarded in the transmission device 203 to the further-processing device 251. The monitoring of the relevant body functions ensues with suitable sensors 221, 222, 223 at the patient 220, with the measured signals being forwarded from a measurement controller 224 to the reception device 204 of the inventive apparatus. The signals are made available to the transmission device 203 for synchronization of the data output.

For example, instruments for monitoring respiration or heart activity can be employed as measurement sensors, for example a respiratory belt, a navigator rod or an instrument for measuring the air quantity inhaled, a pulse measuring device or an electrocardiograph.

Figure 3A:
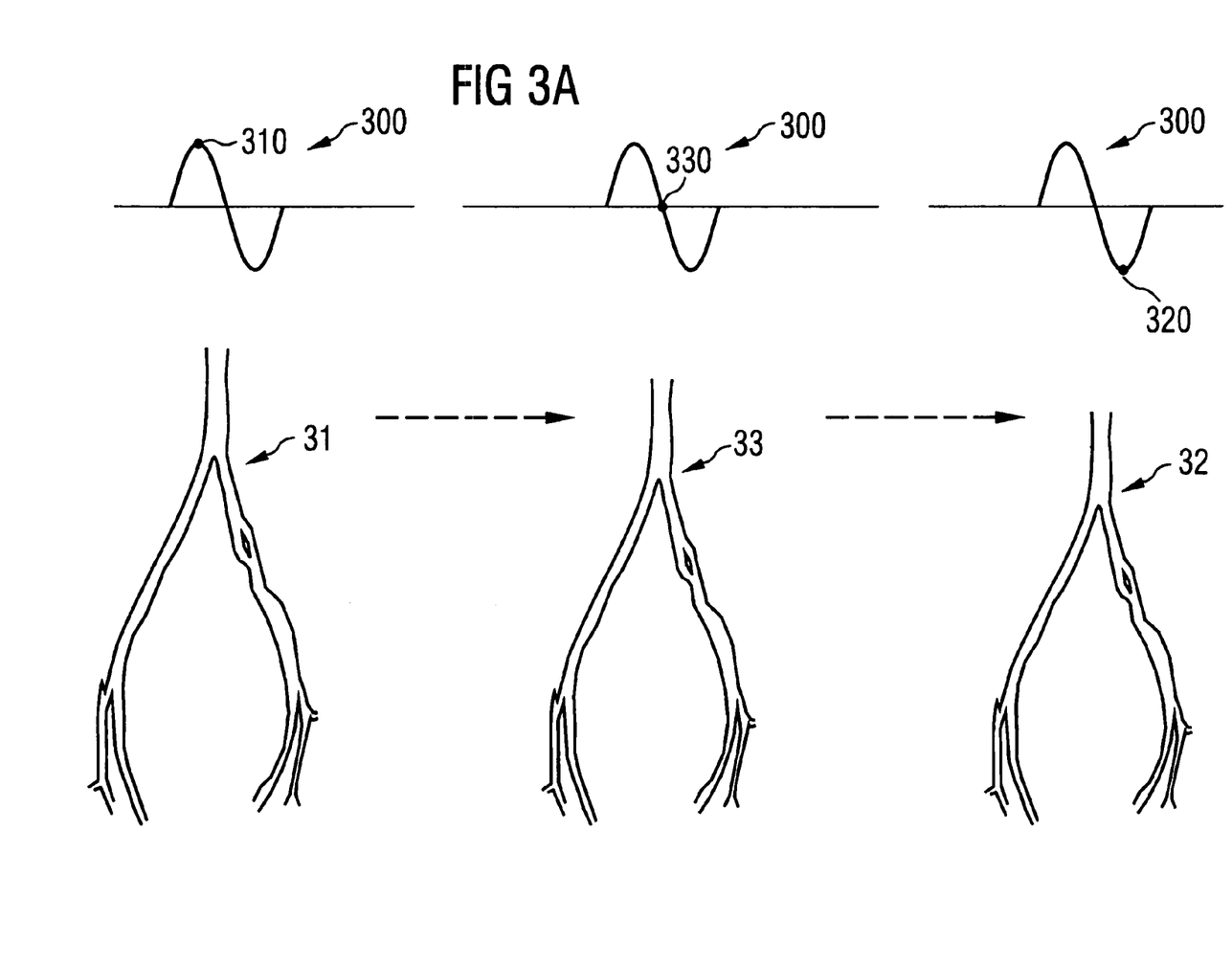
FIG. 3a schematically shows the formation of an intermediate shape from two initial shapes by means of interpolation, suitable for use in the present invention.

FIG. 3a illustrates the interpolation method for calculating intermediate geometries of medical objects using the example of a highly schematically shown angiography image of a vessel tree of the abdominal cavity. The first exposure 31 on which the interpolation is based ensued given complete inhalation, i.e. at the status of final inspiration 310, whereas the second exposure underlying the interpolation ensued given complete exhalation, i.e. at the status of final expiration 320. For illustration, the statuses are marked in the respiratory motion 300 schematically shown as diagram. The intermediate shapes are calculated in that the path of the individual points of the surface is interpolated between the two conditions. Linear interpolation makes it possible to achieve an adaptation of the object geometries that can be realized with adequate precision for many applied purposes and with little calculating outlay. Particularly when the geometries are to be calculated in real time, i.e. synchronously with the currently measured value of the body function, such a method is recommendable. When higher precision is required, a weighted interpolation that takes the time course of the conditions of the body function into consideration is preferred.

Figure 3B:
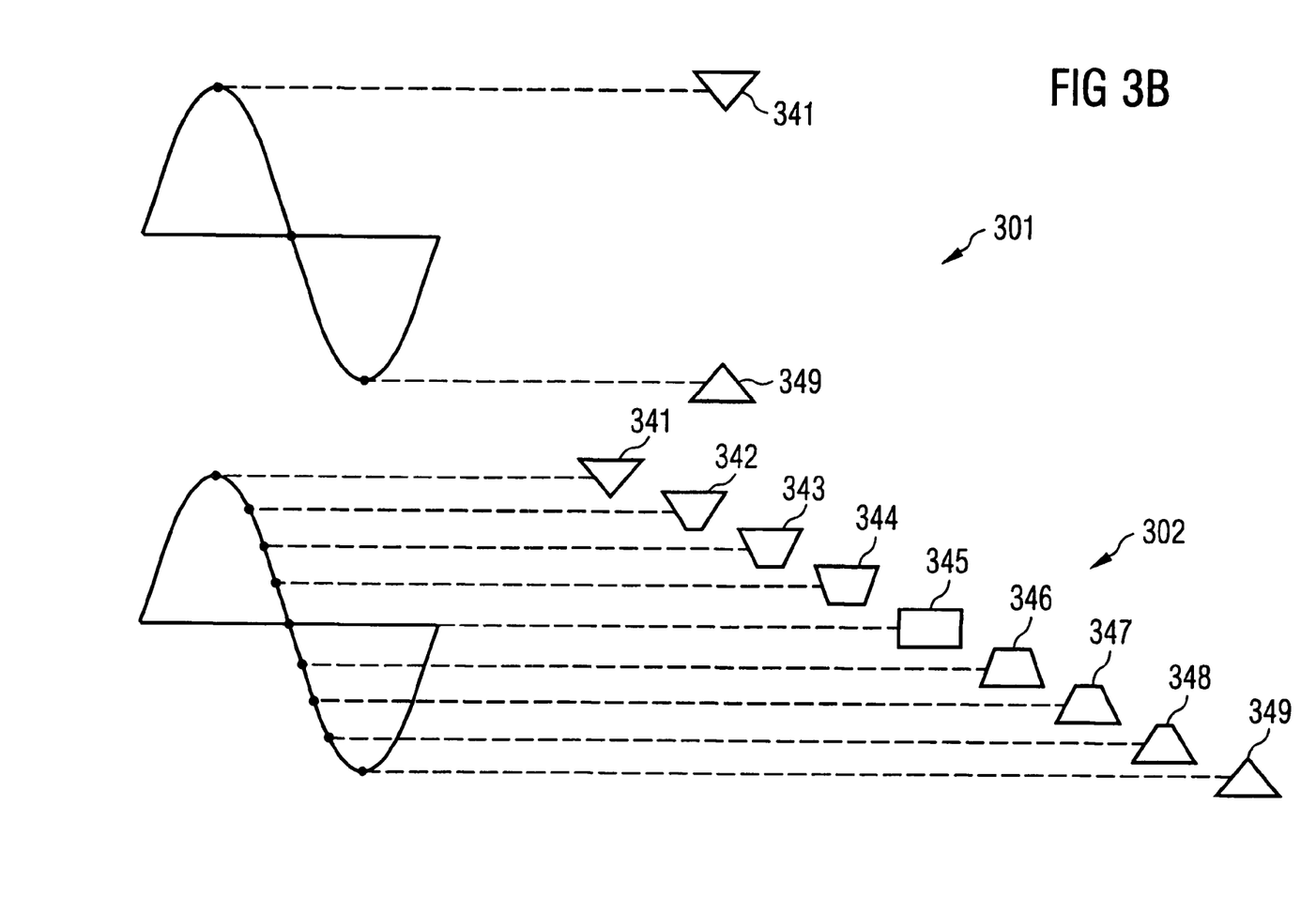
FIG. 3b schematically shows the formation of arbitrary intermediate shapes from two initial shapes by means of morphing, suitable for use in the present invention.

Better results, that can still be achieved with reasonable calculating outlay, can be achieved with an interpolation method known as morphing. This is schematically outlined in FIG. 3b. Morphing is the uniform transformation of a given source geometry 341 into a given target geometry 349. To this end, corresponding points and edges are placed in the source geometry 341 and target geometry 349, these serving as prescription for the geometrical transformation. In the "force field" of the characteristic structures of the geometry that is thereby defined, each point of the geometrical model migrates from its source point to its corresponding target point upon transition from the source condition 341 into the target condition 349 according to this force field. The appertaining intermediate geometry (342, 343, 344, 345, 346, 347, 348) can therefore be calculated and presented for each condition value of the body function in the diagram 302 of FIG. 3b.

Computational simulation of the shape change of medical objects dependent on the body functions influencing them is available as an alternative to the various interpolation methods. For this technique, the geometry of the object need only be known for a defined status value of the body function. Based on the individual configuration of the object, all further conditions of the object can be calculated given knowledge of its change dynamics. For example, models referred to as spring models can be employed as calculation models, which model how points adjacent to specific supporting points shift when these supporting points change in position. The resulting deformation of the surface thus can be simulated in a fashion close to reality.

Figure 4:
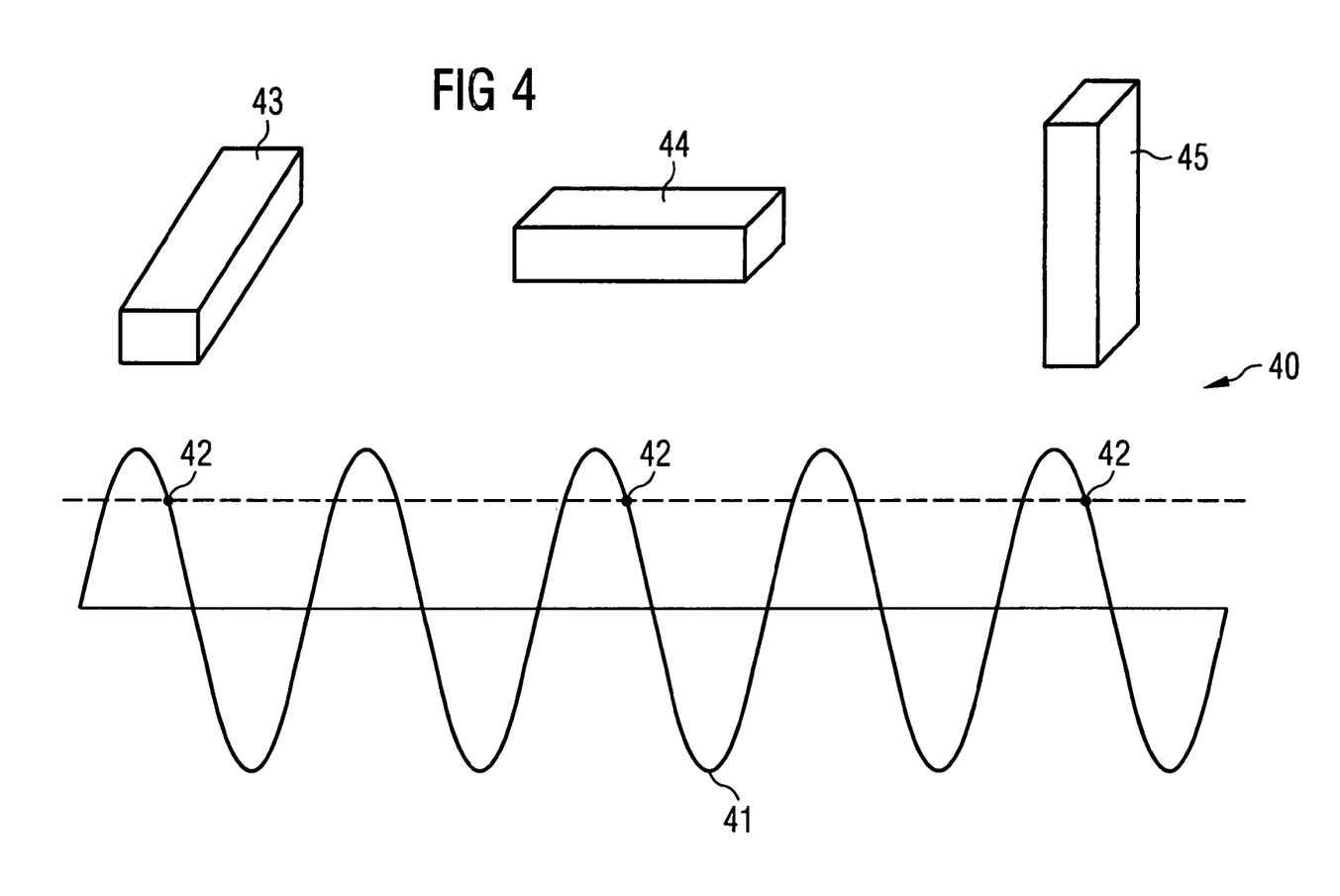
FIG. 4 schematically shows the conditions in order to produce a 3D geometry from a number of 2D descriptions of a medical object.

No medical measuring method that supplies three-dimensional data about the medical object need be employed in order to determine the geometry of a medical object in a defined condition value. The three-dimensional shape of the object can be calculated by the data analysis device 201 of the inventive apparatus 200 from two-dimensional image data as well. In order to obtain a three-dimensional description of the medical object, it suffices to register the object from different sides with a two-dimensional imaging method, as shown in FIG. 4. The various views 43, 44 and 45 of the medical object, a parallelopiped here for the purpose of a simplified illustration, suffice in order to obtain all necessary data for reconstruction of the three-dimensional geometry of the object. As shown in the diagram 40 of the underlying body function 41, the pre-condition for this is that these exposures always ensue given an identical status value 42 of the body function, even if at different times. For example, a number of ultrasound exposures having different orientations can be made at the defined condition values 42 of the body function, and the contours of the object can be segmented from the tomograms obtained by each exposure. A three-imensional object geometry that exactly reflects the three-dimensional medical object in the defined condition value 42 of the body function then can be generated from a number of contours with different orientation segmented in this way.

There are many body functions in the human body with time-reoccurring status values that cause a variation of the geometry of medical objects. Many of these body functions can be measured in a simple way. For example, the activity of the heart can be monitored on the basis of the frequency curve and pressure curve of the pulse. Respiration, together with its basic influence on the shape of the lungs and the neighboring organs, for example, can be tracked by measuring the quantity of air inhaled or by measuring the circumference of the chest. As an alternative, a rod-shaped magnetic resonance excitation can be generated perpendicular to the diaphragm, and the course of the respiration can be acquired via the movement of this navigator rod.

Figure 5:
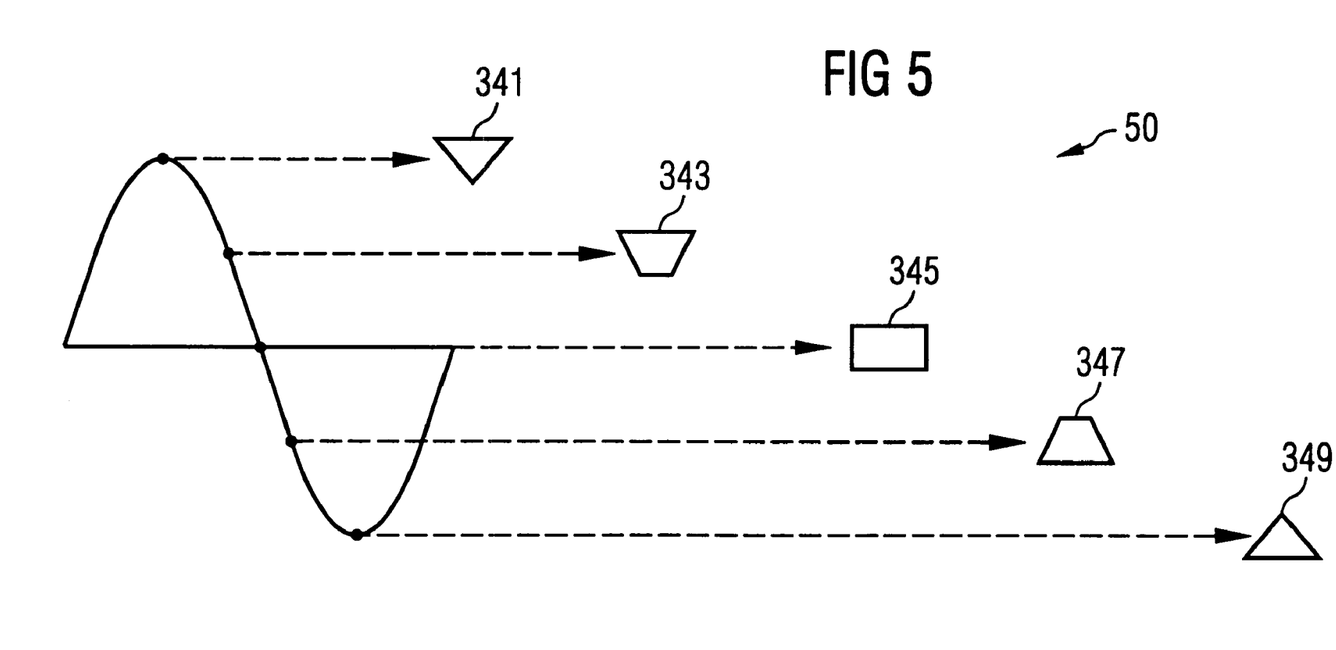
FIG. 5 shows how the current geometry of a medical object is made available corresponding to the current function value in accordance with the invention.

In order to assure that the geometry the inventive apparatus 200 makes available corresponds to the current shape of the medical object it represents, the body function (or body functions if a number of body functions influence the shape of the object) is registered via suitable measuring sensors 221, 222, 223, and the measured signals are forwarded by the measurement controller 224 to the reception device 204 of the inventive apparatus 200. The reception device 204 triggers the output of the geometry corresponding to the current condition values by the transmission unit 203 in conformity with the illustration in diagram 50 of FIG. 5.

The described inventive method can be employed in many situations. For example, the adapted shape of a pre-operatively measured organ can be mixed into a live image of an endoscope during an operation, and thus an excellent geometrical coincidence of pre-operative and intra-operative data can be achieved. This method is referred to as image fusion and also can be applied to ultrasound exposures.

The inventive method also can be utilized in navigation-supported interventions. For example, the current position of an instrument in the patient can be measured and presented in a pre-operatively obtained dataset. In order to be able to represent the position in this dataset exactly, the geometry based on this dataset must be deformed in conformity with the momentary condition of the medical object that underlies it, particularly when the region is subject to a pronounced dynamic deformation, as, for example, is the case in the abdominal cavity or at the heart. If the follow-up of the geometries based on pre-operatively obtained data did not ensue matched to the current situation, the position of the instrument would be presented incorrectly in the image of the medical object. An incorrect presentation of an intervention device such as, for example, a catheter in a pre-operatively measured blood vessel tree can, for example, simulate a dangerous perforation of the vessel wall without such a perforation really being present.

Similar to navigation-supported interventions, an exact definition of positions is also indispensable given robotic controls. Here, as well, the invention offers the indispensable precondition that the position targeted by the robot can be constantly adapted to the current situation.

Although modifications and changes may be suggested by those skilled in the art, it is in the intention of the inventors to embody within the patent warranted hereon all changes and modifications as reasonably and properly come within the scope of their contribution to the art.

The invention claimed is:

1. A method for modeling momentary conditions of a medical object dependent on at least one time-variable body function, comprising the steps of:
   from data acquired by a medical imaging method, calculating in a computer a first geometry of a medical object for at least one first status value of a time-variable body function;
   calculating a plurality of second geometries of said medical object in a computer based on said first geometry of said medical object for a plurality of second status values of said time-variable body function, said second status values being different from said first status value; and
   receiving a currently measured status value of said body function and making one of said second geometries calculated for one of said second status values approximating said currently measured status value.

2. A method as claimed in claim 1 comprising employing data constituting a three-dimensional representation of said medical object as said data obtained by a medical imaging method for calculating said first geometry.

3. A method as claimed in claim 1 comprising employing data constituting a two-dimensional representation of said medical object as said data obtained by a medical imaging method for calculating said first geometry.

4. A method as claimed in claim 1 wherein the step of calculating said second geometry comprises calculating said second geometry by interpolation from two existing geometries of said medical object.

5. A method as claimed in claim 1 wherein the step of calculating said second geometry comprising calculating said second geometry from a calculated model representing physiological behavior of said medical object.

6. A method as claimed in claim 1 wherein the step of calculating said second geometry comprises calculating said second geometry by morphing from an existing geometry of said medical object.

7. A method as claimed in claim 1 comprising employing cardiac activity as said time-variable body function.

8. A method as claimed in claim 1 comprising employing respiration as said time-variable body function.

9. An apparatus for modeling momentary conditions of a medical object dependent on at least one time-variable body function, comprising:
   a data analysis unit supplied with data acquired by a medical imaging method for calculating a first geometry of a medical object for at least one first status value of a time-variable body function;
   a modeling unit for calculating a plurality of second geometries of said medical object based on said first geometry of said medical object respectively for plurality of second status values of said time-variable body function, said second status value being different from said first status value;
   a reception unit which receives a currently measured status value of said body function; and
   a transmission unit, connected to said reception unit and to said modeling unit, which makes one of said second geometries, calculated for one of said second status values approximating said currently measured status value, available during said measurement of said status values of said time-variable body function.

10. An apparatus as claimed in claim 9 wherein said data analysis unit employs data constituting a three-dimensional representation of said medical object as said data obtained by a medical imaging method for calculating said first geometry.

11. An apparatus as claimed in claim 9 wherein said data analysis employs data constituting a two-dimensional representation of said medical object as said data obtained by a medical imaging method for calculating said first geometry.

12. An apparatus as claimed in claim 9 wherein said modeling unit calculates said second geometry by interpolation from two existing geometries of said medical object.

13. An apparatus as claimed in claim 9 wherein said modeling unit calculates said second geometry from a calculated model representing physiological behavior of said medical object.

14. An apparatus as claimed in claim 9 wherein said modeling unit calculates said second geometry by morphing from an existing geometry of said medical object.

15. An apparatus as claimed in claim 9 wherein said reception unit receives a signal representing cardiac activity as said time-variable body function.

16. An apparatus as claimed in claim 9 wherein said reception unit received a signal representing respiration as said time-variable body function.

17. A computer-readable medium encoded with a computer program to model momentary conditions of a medical object dependent on at least one time-variable body function, said computer program, when said computer-readable medium is loaded in a computerized apparatus, causing said computerized apparatus to calculate, from data acquired by a medical imaging method, a first geometry of a medical object for at least one first status value of a time-variable body function, and to calculate a plurality of second geometries of said medical object based on said first geometry of said medical object respectively for a plurality of second status values of said time-variable body function, said second status values being different from said first status value, and, upon obtaining a currently measured status value of said body function, to make one of said second geometries, calculated for one of said status values approximating said currently measured status value, available during said measurement of said status values of said time-variable body function.

* * * * *